United States Patent [19]

Stark et al.

[11] Patent Number: 5,397,538
[45] Date of Patent: Mar. 14, 1995

[54] APPARATUS FOR OPTICALLY EVALUATING COLORIMETRIC COLORATION ZONES ON A CARRIER TO AUTOMATICALLY DETECT GASEOUS AND/OR VAPOROUS COMPONENTS OF A GAS MIXTURE

[75] Inventors: Hartmut Stark, Stockelsdorf; Peter Dreyer, Pansdorf, both of Germany

[73] Assignee: Dragerwerk Aktiengesellschaft, Lübeck, Germany

[21] Appl. No.: 194,262

[22] Filed: Feb. 10, 1994

[30] Foreign Application Priority Data

Feb. 10, 1993 [DE] Germany ............... 43 03 858.1

[51] Int. Cl.[6] ............................................. G01J 1/50
[52] U.S. Cl. ............................................ 422/57; 422/58; 422/83; 422/88; 436/43; 436/44; 436/46
[58] Field of Search ........................... 422/57–58, 422/82.05, 81, 83, 88; 436/43–44, 46

[56] References Cited

U.S. PATENT DOCUMENTS

| 4,913,881 | 4/1990 | Evers ................................ 422/88 |
| 5,069,879 | 12/1991 | Leichnitz et al. ................... 428/447 |
| 5,089,232 | 2/1992 | May .................................. 422/83 |

FOREIGN PATENT DOCUMENTS 58-79141  5/1983  Japan .

*Primary Examiner*—Lyle A. Alexander
*Attorney, Agent, or Firm*—Walter Ottesen

[57] ABSTRACT

The invention is directed to an apparatus for optically evaluating colorimetric coloration zones automatically wherein not only a single testing tube but also a plurality of reaction zones applied one behind the other to a common carrier can be evaluated. The least quantity of indicator substances for the coloration zones is used and an adequate signal intensity with the least possible consumption of power for the optical signal evaluation is attained. At the same time, the sensitivity to faults is reduced. Such an apparatus includes transmission as well as receiving units on a common mounting carrier. The light of the transmitting unit is conducted via a light conductor through the region of the reagent carrier which is transmittent and the coloration of the channel-shaped reaction zones of the carrier is detected in transmission and reflectance.

26 Claims, 3 Drawing Sheets

APPARATUS FOR OPTICALLY EVALUATING COLORIMETRIC COLORATION ZONES ON A CARRIER TO AUTOMATICALLY DETECT GASEOUS AND/OR VAPOROUS COMPONENTS OF A GAS MIXTURE

FIELD OF THE INVENTION

The invention relates to an apparatus for the colorimetric detection of gaseous and/or vaporous components of a gas mixture from the coloration of a channel-shaped reaction zone of which one or more are accommodated on a plate-shaped reagent carrier. The carrier is brought into an evaluation position detected by a signal transmitting unit and a signal receiving unit. In this position, a data field can be read in which is on the reagent carrier. The carrier can be transferred into a measuring position wherein the radiation emitted by a signal transmitting unit onto the reaction zone is detected by the signal receiving unit.

BACKGROUND OF THE INVENTION

A device of this kind is disclosed in U.S. Pat. No. 5,089,232.

The known apparatus is a chip-shaped reagent carrier for several channels which are lined with a colorimetric indicator. The indicator enters into a chemical coloring reaction in the presence of a gaseous and/or vaporous component of the gas mixture which is to be detected. The length of the coloration or the speed with which the coloration advances along the reaction zone is a measure of the quantity or concentration of the component to be detected. The evaluation of each coloration zone takes place in that a row of light sources emit visible or invisible light toward the reaction zone and the reflected light is reflected onto corresponding detectors. The light sources are arranged one behind the other. The signal transmitting unit as well as the signal receiving unit must be adapted to the course of the reaction zone such that a uniform irradiation of the channel path is possible. Only ,small quantities of color indicators are available for the colorimetric display because of the small dimensions of the channels and the reaction zones. The evaluation signal for the receiving unit is correspondingly small. More specifically, the measuring signal is correspondingly susceptible to disturbance components which are caused, for example, by a nonuniform distribution of the indicator material. Likewise, a nonuniform illumination of the reaction zone can lead to a falsification of the measuring signal.

The known carrier with its plurality of channel-shaped reaction zones is introduced into an evaluation unit with the aid of an automatic transport device for the purpose of carrying out a measurement. A data field is read out (for example, in the form of a bar code) during the insertion into the evaluation unit. The data field contains all data necessary for the measurement and evaluation of the measuring signals. The type and number of the reaction zones as well as the correlation which prevails for each reaction zone is provided in a coded form in the data field. The correlation is between the coloration length and concentration of the gaseous components to be detected. The data read in in this manner is transmitted to a control unit and a data processing device (microprocessor). The carrier is placed into a measuring position after evaluation of the data field. In this measuring position, one or more reaction zones are connected to a pump. With the aid of this pump, the gas component to be investigated is pumped through the channel-shaped reaction zones. The reaction zone used for the investigation is brought into the radiation region of the signal transmitting unit and the signal receiving unit for measuring the colorimetric coloration. The transmitting and receiving units are the same which had read out the data field in the evaluation position of the carrier. The indicator colors during the throughflow of the reaction channel in dependence upon the quantity of the gas component to be investigated. The coloration path is detected from the portion of the non-colored reaction zone by the reflection and/or the absorption of different wavelength intensities by the signal receiving unit.

SUMMARY OF THE INVENTION

It is an object of the invention to improve an apparatus of the kind described above so that an adequate signal intensity is obtained with the least possible amount of indicator substance in the coloration zone. It is a further object of the invention to provide such an apparatus wherein the least amount of power is consumed for the signal transmitting unit for the emission of the required quantity of radiation. At the same time, the fault sensitivity for the evaluation is reduced.

The above object is realized in that the carrier, which has a transparent region, has a reagent carrier foil which is likewise transparent and to which the reaction zones are applied. These reaction zones predetermine the course of the channels and each reaction zone has a connection which can be opened and which is provided for the access of the component to be investigated. A transmitting head emits the radiation and defines the signal transmitting unit. The transmitting head is optically coupled to a light conductor which has an emitting surface at the level of the reaction zone. A lateral surface of the reagent carrier is arranged opposite this emitting surface so that radiation can pass through the reaction zone. The signal receiving unit receives the component of radiation transmitted through the reaction zone and is in direct optical communication to the signal transmission unit.

The advantage of the invention is seen essentially in that the length of coloration within the path of the reaction zone can be followed by the signal receiving unit while providing optimal use of the small quantity of indicator substance. A uniform illumination over the length of the reaction zone is ensured because of the continuous transillumination via the emission surface of the light conductor. The distance between the effective radiation surface of the signal transmission unit (the emission surface of the light conductor), on the one side, and the signal sensitive detector surface of the signal receiving unit, on the other side, can be reduced to such a small amount (essentially limited by the thickness of the reagent carrier foil and of the carrier) that an appreciable loss in intensity because of too large a distance of the units from each other is avoided. In this way, a reduced radiation power is adequate and nonetheless a signal with little noise is provided.

The detection of the measuring signal in the transmission measurement for each individual channel makes it furthermore possible to apply different reaction zones to the reagent carrier foil. The simplest form of such a reaction zone is the surface application of the reaction partners necessary for the coloration reaction on the reagent carrier foil, for example, from an emulsion or, it is possible to apply glass capillaries to the reagent carrier foil, which are provided with an inner coating containing the components necessary for the coloring reaction. Any medium or ancillary medium is understood to be a light conductor which can conduct light along a pregiven path from the transmitter to the receiver.

The signal transmitting unit has a LED emitting infrared light as a transmitting head for reading in the data field and a LED radiating in the visible range for the emission of the radiation impinging on the reaction zone. In this way, the signal receiving unit can determine whether the data field is read out in the present measurement sequence or whether there is an evaluation of the length of coloration of the reaction zone. This is achieved with one transmitting unit by means of different wavelengths. The emission characteristic of the infrared LED can be better adapted to the spectral sensitivity of the signal receiving unit by the use of an infrared LED for evaluating the data field. In this way, an essentially improved signal/noise ratio is obtained so that an unmodulated direct scanning of the data field is possible which, otherwise, would be complex and would require the use, for example, of a lock-in amplifier.

The receiving unit is equipped with a detector array in order to detect as completely as possible the length of the reaction zone. The detector array can be either a plurality of individual detectors arranged one behind the other or can be individual detectors assembled into detector arrays. On the other hand, the detector array can have on a common detector carrier light-sensitive regions having a honeycomb or different raster shape. The receiving unit has either a row of a plurality of individual detectors or a detector array which are mounted along the length of the reaction zone. In this way, the entire width of the reaction zone as well as its length can be followed with respect to its coloration. Either the length of the coloration zone or the speed of the advance of the coloration zone can be detected.

If a high position resolution for the detection of the length of the coloration of the reaction zone is wanted, then CCD-sensors can be used as the signal receiving unit. Otherwise, all detectors can be utilized which have a sensitivity characteristic which can be matched to the transmitted wavelength (for example, silicon photodiodes or transistors).

The information transmitted by the detector array can relate to data from the data field or it can be information from the remission measurement or transmission measurement. To ensure that the particular information is transmitted, it is advantageous to provide a diaphragm arrangement in the optical beam path between the emission surface of the light conductor, on the one hand, and the signal receiving unit, on the other hand. This diaphragm arrangement includes a data field diaphragm having diaphragm slits which run in correspondence to the data field configured as a bar code, on the one hand, and run in correspondence to the detector array, on the other hand. The data field diaphragm is made of a material which is opaque to the radiation required for reading out the data field and is transmittent for the radiation required for carrying out the measurement. The data field diaphragm is followed by a measurement field diaphragm viewed in the direction toward the detector array. The measuring field diaphragm has several measuring slits which run perpendicularly to the diaphragm slit but run in a plane parallel to the diaphragm slit of the data field diaphragm. The measuring slits correspond in number to the number of detectors in the detector array and their length corresponds to the width of the reaction zone. The material of the measurement diaphragm is impermeable for the wavelengths for reading out the data field as well as for the wavelength for carrying out a reflectance/transmission measurement at the reaction zone.

If it is assumed for simplicity, that infrared radiation is required for reading out the bar code, then the material of the data field diaphragm is opaque to infrared so that the infrared radiation passes exclusively through the diaphragm slit and impinges on the measurement diaphragm which likewise is impermeable to infrared radiation. The many measurement slits run perpendicular to the diaphragm slit but run in a plane parallel to the data field diaphragm. For this reason, the infrared light strip of the diaphragm slit of the data field diaphragm is subdivided into individual beams corresponding to the number of the measurement slits. Each of the individual light beams impinges on one of the detectors of the detector array.

The various bar codes alternately generate bright and dark beams while the reagent carrier is transported along the detector array. These bright and dark beams are correspondingly directed to the detectors and an alternating irradiation of the detectors is generated which corresponds to the sequence of the bright and dark fields in the bar code. A green measurement radiation is, for example, used if now the reagent carrier is to be read out in transmission or reflection. In the example of a transmission measurement, the green measuring radiation penetrates the reaction zone and exits completely through the entire data field diaphragm transparent for green and can thereby radiate through the entire length of the measurement slits of the measurement diaphragm which is otherwise opaque to green. A resulting beam cross section of green measuring light impinges on each individual detector which cross section in its width corresponds to the individual measuring slit lying opposite the detector and which, in turn, corresponds to the width of the reaction zone. The detector array runs corresponding to the length of the reaction zone. For this reason, each reaction zone is detected by the detector array with a plurality of measurement strips. The closeness of the resulting measurement strips is dependent upon the closeness of the measuring slits in the measurement diaphragm and the closeness of the detectors in the detector array.

Diaphragms having the above-mentioned different transmissibility for infrared or colored visible radiation are supplied by Schott Glaswerke (Mainz, Germany) and made of colored glass under the designation BG 18.

It is advantageous to place the detector array in the apex line of a cylindrically-shaped concave mirror in order to increase the yield of the measuring radiation impinging upon the detector array. The reaction zone extends along the focal point line of the concave mirror. When the reaction zone is transilluminated by the measuring beam, the radiation can be scattered at the transparent material of the reagent carrier foil. The scattered radiation is now reflected on the reflector of the concave mirror and directed back to the reaction zone and from there returned to the detector. In addition to the measuring beam transilluminating the reaction zone, it is in this way possible to also utilize the scattered radiation produced at the colorized carrier of the reaction zone by reflecting the same at the concave mirror to measure the degree of coloration. The scattered radiation through the non-colored transparent region of the reagent carrier foil as well as the scattered radiation after passthrough of the measuring beam through the colored reaction zone is received by the reflector and at least a significant fraction thereof is, in turn, reflected onto the colorized zone and supplied to the detector for evaluation.

The evaluation of the degree of coloration of the reaction zone can be still further improved in that a reflectance light transmitter is mounted additionally in the vicinity of the signal receiver unit. The reflectance light transmitter emits a further measuring beam which is directed onto the reaction zone so that the light, which is reflected by the reaction zone in dependence upon the degree of coloration, is likewise received by the signal receiver unit. In this way, by means of a combination of a transmission measurement and a reflectance measurement, a measuring signal is obtained which is considerably increased above the signal noise and which can be evaluated with reduced error deviation.

The wavelength for the transmission measurement can be the same as that for the reflectance measurement or different wavelengths can be used. The following advantages are provided if light-emitting radiation transmitters of different wavelengths are used: reaction zones having colorimetric indicators colored differently can be evaluated with the wavelength which is most advantageous for that indicator. In advance of making a measurement, the channel to be used can be tested by a suitable test wavelength as to determine whether any coloration has yet occurred. If this is already the case, then the conclusion can be drawn as to a faulty functioning of the indicator, for example, this faulty functioning can be caused by leakage at the channel boundary or because of a defective sealing. Furthermore, during the measuring operation, a color reaction can be obtained in which there is a change of one color to another or there is a conversion and not in a coloration from white to a specific color. Color change reactions of this kind can be better utilized in that the quotient is formed of the signal of the first wavelength with the signal of the second wavelength. A signal of this kind can be more clearly detected than measuring the color shift with a single wavelength which would become noticeable only with a weak change of intensity. The different wavelengths can lie at 500 nanometer and 560 nanometer.

An improved conduction of light is provided by coupling the light conductor with an extension piece optically to the transmitting head. The light is guided via a light bridge to the reaction zone lying opposite the receiving unit. At the reaction zone, the emitting surface is formed as a cylinder lens and is directed toward the receiving unit for transilluminating the reaction surface. In this way, the greatest possible transillumination of the reaction zone is obtained and the configuration of the apparatus is reduced to the smallest possible size.

An advantageous arrangement for a light conductor is seen in that the light conductor is configured as a light strip made of glass or plastic which is transparent for the radiation of the signal transmitting unit. The emitting surface is realized as a front end surface of the light strip. Such a light strip can receive as much as possible of the radiation emitted in a spatial angle which is overlapped by the signal transmitter unit and can transmit this radiation further.

The light conductor can equally well be configured from a bundle of glass fibers to which the signal transmitter unit is optically coupled and the output surface of the bundle is. directed toward the reaction zone.

A further simple embodiment for a light conductor is seen in an arrangement of deflecting mirrors. The transmitting head is positioned in the focal point region of an assigned entrance mirror and the emitting surface is defined by the radiating surface of an exit mirror. An arrangement of this kind is characterized by low weight and simple assembly.

A further simple possibility for the arrangement of a signal transmitter unit and a signal receiver unit comprises positioning the transmitting heads directly opposite to the reaction zone so that the reaction zone is irradiated. The transmitting heads emit the light required for evaluation. The transmitted light impinges then without deflection on the detectors of the signal receiving unit. The reaction zone in this way defines a type of filter in the direct beam path between signal transmitting unit and signal receiving unit. The emitting surface and the light conductor are then defined by an emitting head of the transmitting heads with the emitting head being configured to be shaped as a lens.

The first transmitting head for emitting the radiation required for the colorimetric measurement is mounted on the mounting carrier. In addition to this first transmitting head, a second transmitting head for emitting the radiation required for reading out of the data field is also on the mounting carrier. The measuring radiation can be in the visible range and the radiation for reading out the data field can be in the infrared wavelength range. Each of the transmitting heads is coupled to the light conductor and each of these light conductors is followed by a measuring light bridge for the visible range and a read out light bridge for the infrared radiation range. Both light bridges are joined together and form a common emitting surface lying opposite the receiver unit. The emitting surface is formed as a cylinder lens whereby the reaction zone and the data field can be transilluminated. The sensitivity of the receiver unit is matched to the visible measuring light as well as to the infrared evaluation light.

If a reflectance light transmitter is provided in addition to the signal transmitter unit, then it is advantageous to cause the signal transmitter unit to transmit light of a first wavelength (for example, green at 500 nanometer) and the reflectance light transmitter to transmit light at a second wavelength (for example, yellow at 560 nanometers). With this arrangement, it is possible to definitively provide the transmission-reflectance ratio for both wavelengths for a known reagent carrier and to then calibrate the signal receiving unit so that this ratio remains unchanged when the reagent carrier is not used and that ratio is changed when the reagent carrier is used. If this ratio has changed because of leakage in the reaction zone from the ambient, then an indication for the useability or nonuseability of the overall detecting apparatus is provided.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
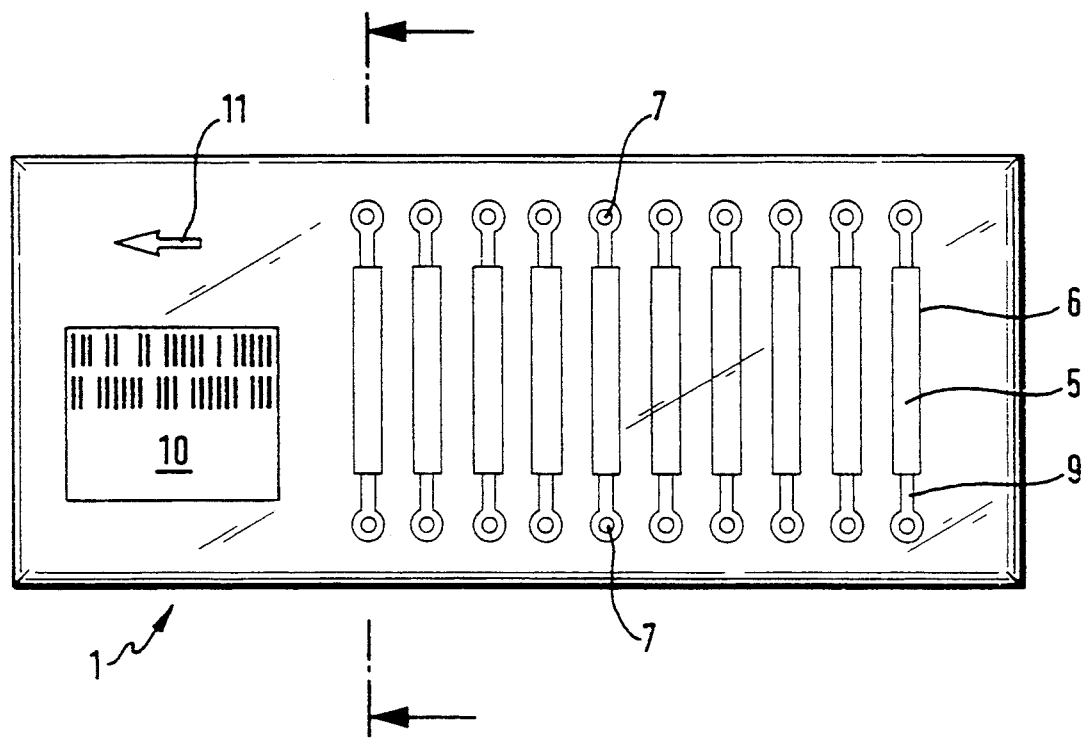
FIG. 1 is a plan view of a plate-shaped reagent carrier having a plurality of reaction channels and a data field.
Figure 2:
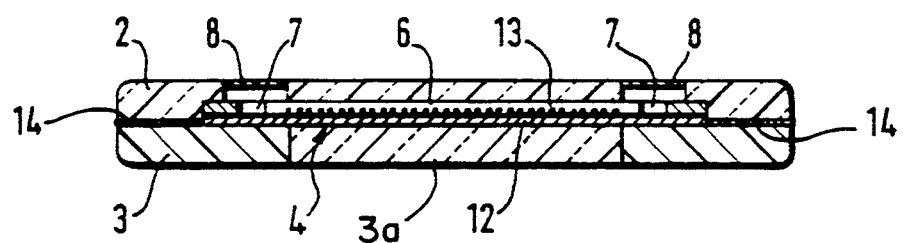
FIG. 2 is a section view taken through the carrier of FIG. 1 along one of the function channels.

FIGS. 1 and 2 show a chip-shaped carrier 1 which comprises a carrier upper part 2 and a carrier lower part 3 as shown in FIG. 2. A composite foil 4 is held between the parts (2, 3). The upper part 2 comprises a transparent plastic material and permits ten parallelly running reaction zones 5 to be freely viewed. Each reaction zone is configured as a base surface for a reaction channel 6. Access openings 7 are provided at the ends of the channel 6 through which the gas mixture to be detected can be drawn by suction with a pump (not shown) or, in the case of an access opening only at one end, the gas mixture can migrate to the reaction zone 5 along the channel 6. The access openings 7 are closed with a seal 8 as shown in FIG. 2 which is punctured for carrying out a measurement. The access openings 7 are each connected to the channels 6 via a channel connection 9.

A data field 10 is printed on the surface of the carrier upper part 2 and provides technical information and instructions for the use of the colorimetric detection device. This information can be read either by the user or by means of an evaluation unit (not shown) with the aid of the data field, for example, in the form of a bar code. A direction arrow 11 indicates which end of the carrier 1 is to be inserted first into the evaluation unit. The data field 10 is read out during the insertion and the information contained therein is transmitted to the evaluation unit. The carrier 1 is inserted so far into the evaluation unit until the first non-used reaction channel 6 reaches the optical evaluation unit.

At the same time, and after the seal 8 is punctured, the pump is connected and the measuring gas to be investigated is drawn through the channel 6 by suction. The reaction zone 5 colors more or less in dependence upon the .content of the gas component in the measuring gas. This is detected by the evaluation unit and processed to a measurement value. An automatic transport to the next-adjacent second channel 6 takes place after evaluation of the first channel 6 is completed. An evaluation of the second channel 6 takes place in the same manner as described above. In this way, up to ten different gas samples can be investigated and measured as required. An arrangement for automatically detecting a data field and the coloration zone of a testing tube is disclosed in U.S. Pat. No. 5,069,879 incorporated herein by reference. The apparatus disclosed in this patent can be utilized also for the carrier 1 but modified as required by the use presented herein.

FIG. 2 is a section view along a channel 6 of the carrier 1 of FIG. 1. The composite foil 4 comprises a reagent carrier foil 12 on which reagent carriers 13 of silica gel are applied. The reagent carriers 13 are impregnated with an indicator and are shown in the form of spherules. The reagent carriers 13 are exposed in the channel 6 to the gas to be investigated.

The carrier upper part 2 has the seal 8 located over the access openings 7. The seal 8 is punctured in order to, for example, connect to a pump (not shown) for pumping the gas. The gas to be detected has access via the access opening 7 to the channel 6 and therewith to the indicator applied to the carrier sperules 13. The carrier upper part 2 is joined about the periphery to the carrier lower part 3 via an adhesive seam 14 whereby the composite foil 4 is held between the two parts (2, 3). The lower carrier part 3 is provided with a window 3a to facilitate transillumination of the composite foil 4 in the apparatus shown in FIGS. 3 to 8.

Figure 3:
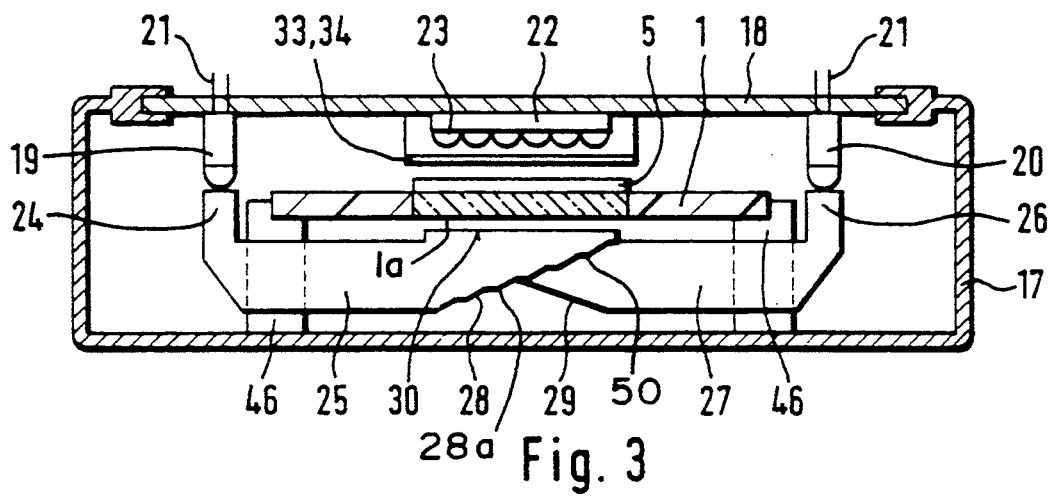
FIG. 3 is a section view of the apparatus for optically evaluating the reaction channels with a light strip made of plastic viewed in the direction of the reaction channel shown in FIG. 2.

In FIG. 3, the apparatus is shown wherein the reagent carrier 1 is shown in section along the length of one of the reaction channels 6 and is brought into its measuring position. The reagent carrier 1 is displaceable by a drive unit (not shown) and is mounted on supports 46. A mounting carrier 18 is arranged in the housing 17 of the apparatus. A transmitting head 19 is mounted on the mounting carrier 18 for the emission of the measuring radiation. A transmitting head 20 is also mounted on the mounting carrier for the emission of the infrared radiation required for the read out of the data field 10. The connection leads 21 of the transmitting heads (19, 20) are shown symbolically and represent the connection to a supply unit (not shown) for electrically operating and driving the transmitting heads (19, 20). A signal receiving unit 22 is attached to the same mounting carrier 18 and is arranged so as to lie opposite the reaction zones to be investigated.

The signal receiving unit 22 comprises a row of detectors 23 which extend along the length of the reaction zone 5. The transmitting head 19 for emission of the measuring radiation is a LED which illuminates in the visible range. The LED is in optical contact with an extension piece 24 of the light conductor 25. The transmitting head 20 is also a LED which illuminates correspondingly for the emission of infrared light. The LED is connected to an extension 26 of a light conductor 27 for passing the infrared radiation. The light conductor 25 for the measuring radiation ends in a reflecting surface 28 for the measuring radiation. This reflecting surface 28 comprises a plurality of individual inclined reflecting surfaces 28a ascending in a step-like manner. These individual surfaces 28a are matched in position and reflective angle so that an individual surface lies opposite a corresponding one of the detectors 23 of the signal receiving unit 22 when viewed with respect to radiation reflected thereto.

In a like manner, the light conductor 27 for the infrared radiation is provided with a smooth beveled reflecting surface 29 at its end lying opposite the extension 26 whereby the entire infrared radiation radiates through the data field 10 when the carrier 1 is in its initial evaluation position. The reflecting surface 28 as well as the reflecting surface 29 direct the radiation of the transmitting heads (19, 20) in the direction of a cylinder-shaped emitting surface 30 which, in its extent, corresponds to the length of the reaction zone 5.

The light conductors 25 and 27 conjointly define an interface 50 whereat the light conductors mutually abut with no change in the index of refraction. Accordingly, the cylinder-shaped emitting surface 30 is common the radiation of both transmitting heads (19, 20).

Figure 4:
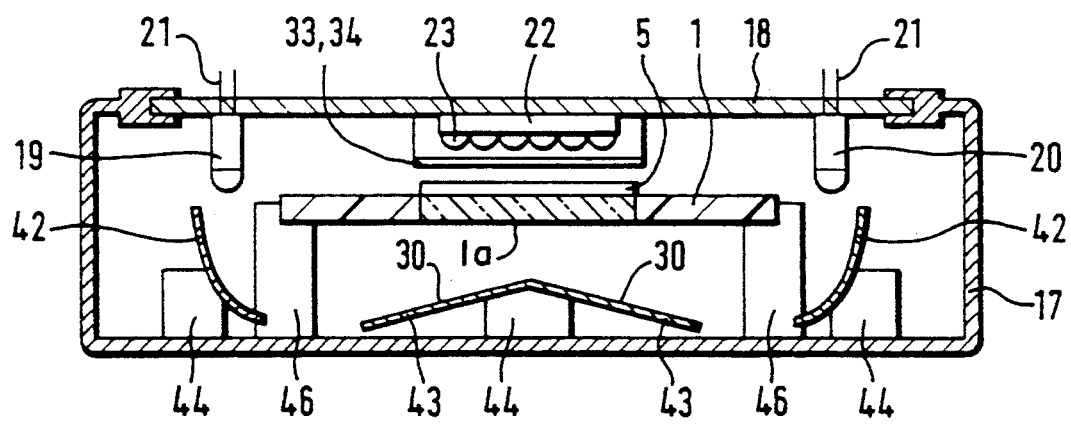
FIG. 4 is another embodiment of the apparatus for optically evaluating the reaction channels with an arrangement of deflecting mirrors.

A mirror arrangement for deflecting the radiation from the transmitting heads (19, 20) to the reaction zone 5 of the reagent carrier 1 is shown in FIG. 4. The same symbols appearing in FIG. 3 are used in FIG. 4. The measuring radiation from the transmitting head 19 and the infrared radiation from the transmitting head 20 are directed to respective inlet mirrors 42 arranged with respect thereto. The inlet mirrors 42 are each curved so as to be concave so that the transmitting heads (19, 20) are positioned in respective focal point regions of the inlet mirrors 42.

The radiation reflected by the mirrors 42 impinges on respective reflectors 43 having reflective surfaces which operate as emitting surfaces 30. These emitting surfaces direct the radiation in transmission through the reagent carrier 1, the reaction zone 5 and the diaphragms (33, 34) to the detectors 23. The mirrors 42 and reflectors 43 are attached to a mirror mount 44.

Figure 5:
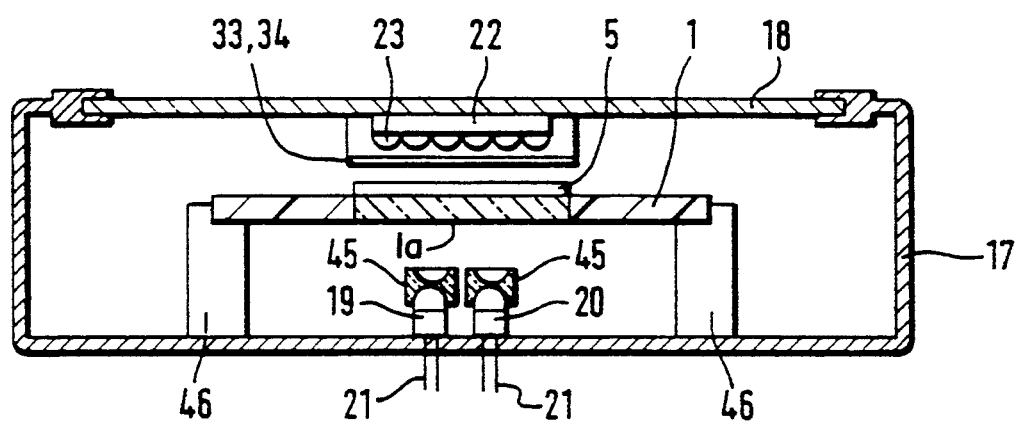
FIG. 5 is another embodiment of the apparatus of the invention with an arrangement of a transmitting unit and a signal receiving unit lying opposite each other.

A further simple arrangement of the transmitting heads (19, 20), on the one hand, and the signal receiving unit 22, on the other hand, is shown in FIG. 5. Here too, identical components of FIGS. 3 and 4 are shown with the same reference numerals.

In contrast to FIGS. 3 and 4, the transmitting heads (19, 20) are, however, mounted on the base surface of the housing 17 at the side of the reagent carrier 1 facing away from the signal receiving unit 22. The radiation is thereby directed in transmission through the reaction zone 5 to the signal receiving unit 22. The light conductor and the emission surface are defined by the lens-configuration of the emission head 45 of the transmitting heads (19, 20).

Figure 6:
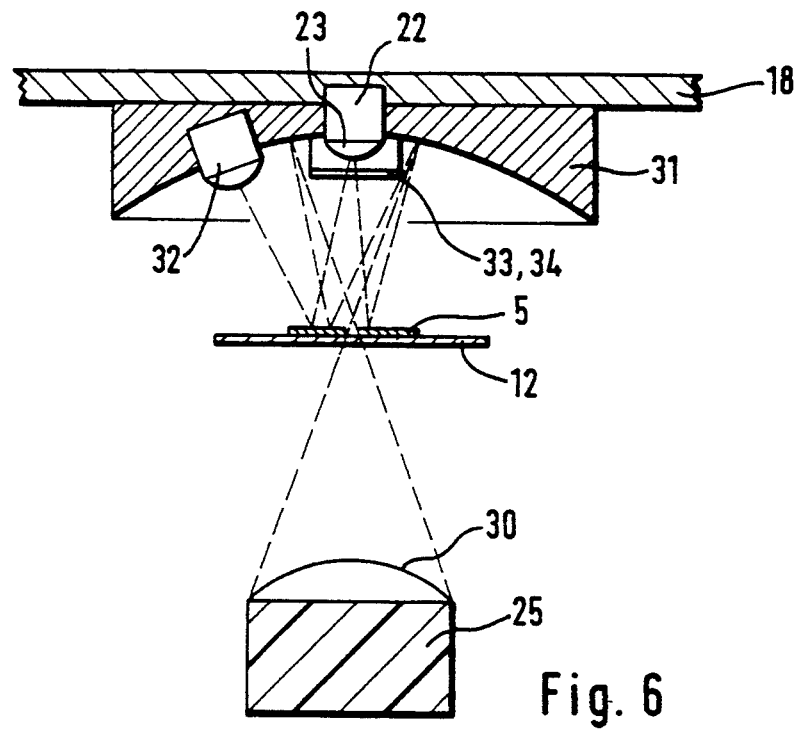
FIG. 6 is another view of the apparatus in the longitudinal direction of the reaction channel of FIG. 2 with an additional concave mirror.

In FIG. 6, several details of FIG. 3 are shown transversely to the reaction channel 6 of FIG. 2 as they are required for the detection of the measuring radiation. A cylinder-shaped concave mirror 31 is mounted on tile mounting carrier 18 in addition to the signal receiving unit 22. The signal receiving unit is embedded in the form of a detector array 22 in the apex line of the concave mirror 31. Likewise, a reflectance light transmitter 32 is provided on the mounting carrier 18 and penetrates the concave mirror 31. The reflectance light transmitter 32 comprises a LED defining a light strip or a LED array which emits radiation in the visible range onto the reaction zone 5.

For the sake of simplicity, the reaction zone 5 is applied to the reagent carrier foil 12. The remaining components of the carrier 1 which are necessary for supporting the reagent carrier foil 12 as well as the other foils of the Composite foil 4 are here omitted.

The emitting surface of the light conductor 25 is formed to a cylinder lens 30 and emits measuring radiation in a path as shown by the broken lines in FIG. 6 with the measuring radiation passing through the reagent carrier foil 12 and through the reaction zone 5 disposed thereon. This transmission radiation is projected, on the one hand, directly onto the signal receiving unit 22 and, on the other hand, is scattered by the surface of the reaction zone 5 and by the reagent carrier foil 12 and impinges upon the concave mirror 31 adjacent to the signal receiving unit 22. This scattered radiation would have been lost for evaluation of the coloration in the reaction zone 5 but is instead reflected back because of the reflection at the concave mirror 31 and impinges on the reaction zone 5 and a certain portion thereof is directed back to the signal receiving unit 22. In this way, the yield of the transmission radiation is increased for utilizing a measuring signal of the coloration along the reaction zone 5 with the reaction zone being investigated at a given time point. The reflection light transmitter 32 transmits additional measuring radiation either of a different wavelength or of the same wavelength as the transmission radiation. The reflectance light transmitter 32 is likewise directed onto the reaction zone 5 whereby the reflectance radiation is reflected onto the same signal receiving unit 22. Here too the same effect with respect to scattered radiation occurs with reflectance as it is explained above for transmission measurement. In the embodiment shown, the reflectance light transmitter 32 is shown in combination with the concave mirror 31. However, the use of the reflectance light transmitter 32 is not dependent upon whether the concave mirror 31 is provided or not.

Figures 7, 8:
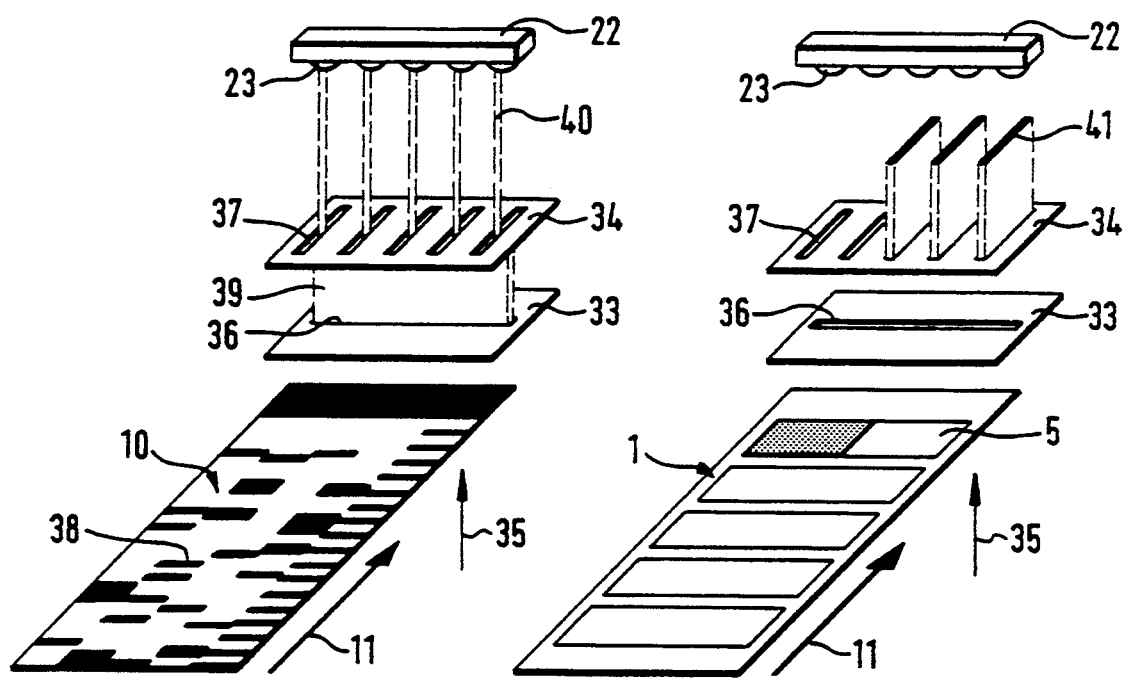
FIG. 7 is a schematic representation of the operation of the radiation diaphragms for the data field read out; and, FIG. 8 is a schematic of the operation of the radiation diaphragms for signal detection.

The operation of a data field diaphragm 33 as well as a measuring diaphragm 34 is shown in FIGS. 7 and 8 schematically wherein only the necessary details of FIGS. 1 to 6 are included.

In FIG. 7, the situation is shown wherein the reagent carrier 1 is brought into the read-out position. The data field 10 is shown in the form of a bar code and is pushed through in the direction of the directional arrow 11 below the data field diaphragm 33. The infrared light transmitted by the transmitting head 20 transilluminates the data field 10 in the direction of the light arrow 35. The data field diaphragm 33 comprises material opaque to infrared light so that infrared light passes through the data field diaphragm 33 only through a diaphragm slit 36.

The diaphragm slit 36 corresponds in its linear extent to the width of the data field 10. The infrared light passing through the diaphragm slit 36 impinges thereafter onto the measuring field diaphragm 34 which likewise is opaque to infrared light. Several measuring slits 37 are formed in the measuring field diaphragm 34 and run at right angles to the diaphragm slit 36 of the data field diaphragm 33. The measuring field diaphragm 34 is parallel to the data field 10 and to the data field diaphragm 33.

The positions of the measuring slits 37 are on the one hand aligned to the code strips 38 of the data field 10 and one measuring slit 37 is provided for each code strip 38. On the other hand, the measuring slits 37 are aligned to respective detectors 23 of the signal receiving unit 22. The single band of radiation 39 passes through the diaphragm slit 36 and is subdivided into a plurality of radiation strips 40 with the number thereof corresponding to the number of measurement slits 37. This is achieved by the crossed arrangement of the diaphragm slits 36 on the one hand and the measuring slits 37 on the other hand. Each individual radiation strip 40 impinges on the detector 23 corresponding thereto. Corresponding radiation strips 40 are generated in dependence upon the presence of a bright field or a dark field on the code strip 38 and are directed toward the detectors 23.

A reaction zone 5 is shown schematically in FIG. 8 and is blackened to the extent of one half thereof. The blackened region represents the coloration of the reaction zone 5. In the measurement position of the carrier 1 shown here, green measuring radiation is directed from transmitting head 19 in correspondence to the light arrow 35 through the reaction zone 5 in transmission. The transmission radiation 35 so obtained impinges on the data field diaphragm 33 which is transmittent for the green measuring radiation so that this diaphragm 33 shows no diaphragm action with reference to the measuring radiation. Thus, the entire measuring radiation 35 impinges on the measuring field diaphragm 34 which, in turn, is non-transmittent for the green measuring radiation 35. A row of measurement radiation bands 41 is generated because the length of the measuring slits 37 corresponds to the width of the reaction zone 5. The measuring radiation bands 41 pass through those measuring slits 37 which lie opposite the non-darkened region of the reaction zone 5. Corresponding detectors of the detector array 23 are charged with measuring radiation 35 in correspondence to the number of measuring radiation bands 41 and generate a measuring signal which corresponds to the length of the coloration on the reaction zone 5.

In the embodiment shown, two of the measuring slits 37 are not transilluminated because they lie opposite the colored region of the reaction zone 5 which is more or less opaque to the measuring radiation. For the case wherein the colored region of the reaction zone 5 is only partially transmissive for the measuring radiation, all measuring slits 37 are transilluminated; however, the radiation through those measuring slits 37 which lie opposite the colored region of the reaction zone 5 is attenuated with respect to its intensity. That measuring radiation however which passes through such measuring slits 37, which do not lie opposite the colored region of the reaction zone 5, is unattenuated with respect to its intensity. In this case too, because of the change of the intensity along the detectors, a signal is generated corresponding to the coloration zone by the signal receiving unit 22.

Several detectors 23 are mounted as a detector array one behind the other following the course of the reaction zone 5. In this way, not only the length of the coloration of the reaction zone 5 is measured as shown in FIG. 8 but also the time-dependent course of the advance of the coloration can be followed. For this purpose, only the number of detectors 23 must be determined from a signal processing unit (not shown) or an inquiry can be made as to the time span elapsed between the irradiation of one detector 23 to the irradiation of the next detector.

It is understood that the foregoing description is that of the preferred embodiments of the invention and that various changes and modifications may be made thereto without departing from the spirit and scope of the invention as defined in the appended claims.

What is claimed

1. An arrangement for colorimetrically detecting a gaseous and/or vaporous component of a gas mixture, the arrangement comprising:
    a plate-shaped reagent device including: a carrier having transparent regions; a reagent carrier foil mounted in said carrier and likewise having a transparent region; a color indicator containing reagents for entering into a color reaction with said component; said color indicator being disposed on said reagent carrier foil along a predetermined path thereon to define a reaction zone having a predetermined width; and, access means for facilitating the passage of said gas mixture to said reaction zone to permit said component to enter into a color reaction with said color indicator in said reaction zone; and,
    an apparatus for detecting said component with reference to the coloration of said reaction zone, the apparatus including:
    a housing for receiving said reagent device therein at a measuring position wherein said reaction zone can be measured;
    radiation emitting transmitter means mounted on said housing for emitting radiation;
    said carrier having a data field formed thereon and being receivable in said housing at a read-in position wherein the data of said data field can be read in;
    light conducting means optically coupled to said transmitter means and having an emitter surface below said reagent device opposite said reaction zone when said reagent device is in said measuring position and opposite said data field when said reagent device is in said read-in position;
    receiver means mounted above said reaction zone so as to be optically coupled to said emitter surface for receiving said radiation transmitted through said reaction zone and said data field;
    said transmitter means including: a first transmitter for emitting a first radiation required to transilluminate said reaction zone and for making measurements along said reaction zone when said reagent device is in said measuring position; and, a second transmitter for emitting a second radiation to transilluminate said data field when said reagent device is in said read-in position;
    said receiver means including a plurality of detectors defining a detector array corresponding to said path of said reaction zone;
    a data field diaphragm interposed between said receiver means and said emitter surface;
    said data field diaphragm defining a plane and having a diaphragm slit formed therein so as to extend in correspondence to said data field as well as to said detector array;
    said data field diaphragm being made of a material transmittent for said first radiation and opaque to said second radiation;
    a measuring field diaphragm having a plurality of measuring slits formed therein extending perpendicularly to said diaphragm slit of said data field diaphragm;
    said measuring field diaphragm being disposed in a plane parallel to said plane of said data field diaphragm and being interposed between said data field diaphragm and said receiver means;
    said measuring slits corresponding in number to the number of said detectors and each of said measuring slits having a length corresponding to said width of said reaction zone; and,
    said measuring field diaphragm being made of a material opaque to said first radiation as well as to said second radiation.

2. The arrangement of claim 1, said data field being a bar code; said carrier being receivable in said housing at a read-in position wherein the data of said bar code can be read in; said light conducting means comprising a first deflecting mirror for receiving and deflecting said radiation; said first deflecting mirror defining a first focal point and said transmitter means being a first transmitter disposed in said focal point; and, a first output mirror defining said emitter surface by deflecting said radiation onto said reagent device; and, said apparatus further comprising a second deflecting mirror defining a second focal point; a second transmitter disposed in said second focal point; and, a second output mirror for deflecting the radiation from said second transmitter to transilluminate said bar code.

3. The arrangement of claim 1, said data field being a bar code; said first transmitter being a first LED for emitting visible radiation for transilluminating said reaction zone; and, said second transmitter being a second LED for emitting infrared light for transilluminating said bar code.

4. The arrangement of claim 1, said plurality of detectors being arranged in a row to define a detector array corresponding to said path of said reaction zone; and, a mounting carrier for accommodating said detectors thereon.

5. The arrangement of claim 1, said data field being a bar code; comprising a first light conductor having a first emitter surface defining said emitter surface; and, a second light conductor having a second emitter surface below said reagent device opposite said bar code to transilluminate said bar code when said reagent device is in said read-in position with said second radiation from said second transmitter; said housing having a base wall and said first and second transmitters being mounted on said base wall; said first light conductor and said first emitting surface conjointly defining a first emitting head for directing said first radiation through said reaction zone directly to said receiver means; and, said second light conductor and said second emitting surface conjointly defining a second emitting head for directing said read-out radiation through said bar code directly to said receiver means.

6. The arrangement of claim 1, said light conducting means comprising a light conductor having a first end optically coupled to said transmitter means and a second end defining said emitter surface for emitting said first and second radiations toward said receiver means.

7. The arrangement of claim 1, said first transmitter including a plurality of transmitting heads transmitting said first radiation at respective wavelengths.

8. The arrangement of claim 1, said first radiation having a first wavelength and said second radiation having a second wavelength different from said first wavelength.

9. The arrangement of claim 8, said first wavelength being 500 nanometer corresponding to green light and said second wavelength being 560 nanometer corresponding to yellow light.

10. The arrangement of claim 1, said data field being a bar code; said light conducting means including a first light conductor optically coupled to said first transmitter; and, a second light conductor having a first end optically coupled to said second transmitter and a second end optically coupled to said first light conductor and said emitter surface so as to permit said second radiation to transilluminate said bar code when said reagent device is in said read-in position with second radiation from said second transmitter also reaching said receiver means from said emitter surface; and, said first and second light conductors having first and second extension pieces so as to permit said plate-shaped reagent device to be disposed in a plane between said emitting surface on one side of said reagent device and said receiver means on the other side of said reagent device.

11. The arrangement of claim 10, said first and second light conductors being respective light conducting strips transparent to the radiation of said first and second transmitters; said light conducting strips being made of plastic or glass; and, said first and second light conductors being optically joined so as to cause said emitter surface to be common to both of said light conducting strips.

12. The arrangement of claim 10, said apparatus further comprising a cylindrical concave mirror defining an apex line and a focal line; said concave mirror being positioned in said housing above said reaction zone so as to cause said focal line to lie in said reaction zone; and, said detector array being mounted in said mirror along said apex line.

13. The arrangement of claim 10, further comprising a mounting carrier in said housing; said first transmitter being mounted on said mounting carrier and being configured to emit said first radiation required for colorimetric measurement of said reaction zone and said first radiation having a wavelength in the visible wavelength range; said second transmitter also being mounted on said mounting carrier and being configured to emit said second radiation required for reading out said bar code and said first radiation having a wavelength in the infrared wavelength range; said first and second transmitters being separately optically coupled to corresponding ones of said first and second light conductors; said first light conductor having a first reflection surface means for reflecting said first radiation toward said reaction zone when said reagent device is in said measuring position; said second light conductor having second surface reflection means for reflecting said second radiation toward said bar code when said reagent device is in said read-out position; and, said receiver means having a sensitivity matched to said first radiation as well as to said second radiation.

14. An arrangement for colorimetrically detecting a gaseous and/or vaporous component of a gas mixture, the arrangement comprising:

a plate-shaped reagent device including: a carrier; a color indicator containing reagents for entering into a color reaction with said component; said color indicator being disposed on said reagent carrier along a predetermined path thereon to define a reaction zone having a predetermined width; and, access means for facilitating the passage of said gas mixture to said reaction zone to permit said component to enter into a color reaction with said color indicator in said reaction zone; and, an apparatus for detecting said component with reference to the coloration of said reaction zone, the apparatus including:

a housing for receiving said reagent device therein at a measuring position wherein said reaction zone can be measured;

radiation emitting transmitter means mounted on said housing for emitting a radiation;

said carrier having a data field formed thereon and being receivable in said housing at a read-in position wherein the data of said data field can be read in;

light conducting means optically coupled to said transmitter means and having an emitter surface below said reagent device opposite said reaction zone when said reagent device is in said measuring position and opposite said data field when said reagent device is in said read-in position for transilluminating said reaction zone and said data field;

receiver means mounted above said reaction zone so as to be optically coupled to said emitter surface for receiving said first radiation transmitted through said reaction zone and said data field;

a cylindrically-shaped concave mirror defining an apex line and a focal line; said concave mirror being positioned in said housing above said reaction zone so as to cause said focal line to lie in said reaction zone; and, said receiver means being mounted in said concave-mirror along said apex line; and, a reflectance light transmitter for emitting additional radiation directed onto said reaction zone so that light is reflected from said reaction zone in dependence upon the degree of coloration thereof and received by said receiver means.

15. The arrangement of claim 14 said data field being a bar code; said transmitter means including: a first transmitter for emitting a first radiation required to transilluminate said reaction zone and for making measurements along said reaction zone when said reagent device is in said measuring position; and, a second transmitter for emitting a second radiation to transilluminate said data field when said reagent device is in said read-in position;

said receiver means including a plurality of detectors defining a detector array corresponding to said path of said reaction zone; and, said arrangement further including:

a data field diaphragm interposed between said receiver means and said emitter surface;

said data field diaphragm defining a plane and having a diaphragm slit formed therein so as to extend in correspondence to said bar code as well as to said detector array;

said data field diaphragm being made of a material transmittent for said first radiation and opaque to said second radiation;

a measuring field diaphragm having a plurality of measuring slits formed therein extending perpendicular to said diaphragm slit of said data field diaphragm;

said measuring field diaphragm being disposed in a plane parallel to said plane of said data field diaphragm and being interposed between said data field diaphragm and said receiver means;

said measuring slits corresponding in number to the number of said detectors and each of said slits having a length corresponding to said width of said reaction zone; and, said measuring diaphragm being made of a material opaque to said first radiation as well as to said second radiation.

16. The arrangement of claim 15, said plurality of detectors being arranged in a row to define said*detector array corresponding to said path of said reaction zone; and, a mounting carrier for accommodating said detectors thereon.

17. The arrangement of claim 15, said light conducting means comprising a light conductor having a first end optically coupled to said transmitter means and a second end defining said emitter surface for emitting said first and second radiations toward said receiver means.

18. The arrangement of claim 15, said first and second light conductors being respective light conducting strips transparent to the radiation of said first and second transmitters; said light conducting strips being made of plastic or glass; and, said first and second light conductors being optically joined so as to cause said emitter surface to be common to both of said light conducting strips.

19. The arrangement of claim 15, said carrier being receivable in said housing at a read-in position wherein the data of said bar code can be read in; said light conducting means comprising a first deflecting mirror for receiving and deflecting said radiation; said first deflecting mirror defining a first focal point and said transmitter means being a first transmitter disposed in said focal point; and, a first output mirror defining said emitter surface by deflecting said radiation onto said reagent device; and, said apparatus further comprising a second deflecting mirror defining a second focal point; a second transmitter disposed in said second focal point; and, a second output mirror for deflecting the radiation from said second transmitter to transilluminate said bar code.

20. The arrangement of claim 15, said first transmitter being a first LED for emitting visible radiation for transilluminating said reaction zone; and, said second transmitter being a second LED for emitting infrared light for transilluminating said bar code.

21. The arrangement of claim 15, said first transmitter including a plurality of transmitting heads transmitting said first radiation at respective wavelengths.

22. The arrangement of claim 15, said light conducting means comprising: a first light conductor having a first emitter surface defining said emitter surface; and, a second light conductor having a second emitter surface below said reagent device opposite said bar code to transilluminate said bar code when said reagent device is in said read-in position with said second radiation from said second transmitter; said housing having a base wall and said first and second transmitters being mounted on said base wall; said first light conductor and said first emitting surface conjointly defining a first emitting head for directing said first radiation through said reaction zone directly to said receiver means; and, said second light conductor and said second emitting surface conjointly defining a second emitting head for directing said read-out radiation through said bar code directly to said receiver means.

23. The arrangement of claim 15, said light conducting means including a first light conductor optically coupled to said first transmitter; and, a second light conductor having a first end optically coupled to said second transmitter and a second end optically coupled to said first light conductor and said emitter surface so as to permit said second radiation to transilluminate said data field when said reagent device is in said read-in position with said second radiation from said second transmitter also reaching said receiver means from said emitter surface; and, said first and second light conductors having first and second extension pieces so as to permit said plate-shaped reagent device to be disposed in a plane between said emitting surface on one side of said reagent device and said receiver means on the other side of said reagent device.

24. The arrangement of claim 23, further comprising a mounting carrier in said housing; said first transmitter being mounted on said mounting carrier and being configured to emit said first radiation required for colorimetric measurement of said reaction zone and said first radiation having a wavelength in the visible wavelength range; said second transmitter also being mounted on said mounting carrier and being configured to emit said second radiation required for reading out said bar code and said first radiation having a wavelength in the infrared wavelength range; said first and second transmitters being separately optically coupled to corresponding ones of said first and second light conductors; said first light conductor having a first reflection surface means for reflecting said first radiation toward said reaction zone when said reagent device is in said measuring position; said second light conductor having second surface reflection means for reflecting said second radiation toward said bar code when said reagent device is in said read-out position; and, said receiver means having a sensitivity matched to said first radiation as well as to said second radiation.

25. The arrangement of claim 15, said first radiation having a first wavelength and said second radiation having a second wavelength different from said first wavelength.

26. The arrangement of claim 23, said first wavelength being 500 nanometer corresponding to green light and said second wavelength being 560 nanometer corresponding to yellow light.

* * * * *

UNITED STATES PATENT AND TRADEMARK OFFICE
CERTIFICATE OF CORRECTION

PATENT NO. : 5,397,538

DATED : March 14, 1995

INVENTOR(S) : Hartmut Stark and Peter Dreyer

It is certified that error appears in the above-identified patent and that said Letters Patent is hereby corrected as shown below:

In the title page, under "Assignee", item [73]: delete "Dragerwerk Aktiengesellschaft" and substitute -- Drägerwerk Aktiengesellschaft -- therefor.

In column 1, line 41: between "Only" and "small", delete ",".

In column 6, line 4: between "is" and "directed", delete ".".

In column 6, line 68: delete "function" and substitute -- reaction -- therefor.

In column 9, line 39: delete "tile" and substitute -- the -- therefor.

In column 9, line 53: delete "Composite" and substitute -- composite -- therefor.

In column 11, line 51: after "claimed", insert -- is: --.

In column 13, line 17: between "code;" and "comprising", insert -- said light conducting means --.

In column 15, line 8: delete "concave-mirror" and substitute -- concave mirror -- therefor.

In column 15, line 15: between "14" and "said", insert -- , --.

UNITED STATES PATENT AND TRADEMARK OFFICE
CERTIFICATE OF CORRECTION

PATENT NO. : 5,397,538

DATED : March 14, 1995

INVENTOR(S) : Hartmut Stark and Peter Dreyer

It is certified that error appears in the above-identified patent and that said Letters Patent is hereby corrected as shown below:

In column 15, line 53: delete "said*detector" and substitute -- said detector -- therefor.

Signed and Sealed this

Thirtieth Day of May, 1995

Attest:

BRUCE LEHMAN

Attesting Officer    Commissioner of Patents and Trademarks